United States Patent
Carson

(10) Patent No.: US 6,188,930 B1
(45) Date of Patent: Feb. 13, 2001

(54) METHOD AND APPARATUS FOR PROVIDING LOCALIZED HEATING OF THE PREOPTIC ANTERIOR HYPOTHALAMUS

(75) Inventor: Gary Allen Carson, Golden, CO (US)

(73) Assignee: Medivance Incorporated, Louisville, CO (US)

( * ) Notice: Under 35 U.S.C. 154(b), the term of this patent shall be extended for 0 days.

(21) Appl. No.: 09/392,971

(22) Filed: Sep. 9, 1999

Related U.S. Application Data

(60) Provisional application No. 60/099,965, filed on Sep. 11, 1998.

(51) Int. Cl.⁷ .......................................... A61F 2/00
(52) U.S. Cl. ......................... 607/101; 607/102; 607/156; 606/32; 606/33; 606/34; 606/41; 128/898
(58) Field of Search ............................. 607/96, 102, 116, 607/122, 156, 157; 606/32, 33, 34, 41, 45, 46, 48–50, 28; 128/898

(56) References Cited

U.S. PATENT DOCUMENTS

| | | | |
|---|---|---|---|
| 4,002,175 | 1/1977 | Brainard et al. | 128/399 |
| 4,425,917 | 1/1984 | Kuznetz | 128/403 |
| 4,660,572 * | 4/1987 | Maruyama et al. | 607/154 |
| 4,781,193 | 11/1988 | Pagden | 128/402 |
| 4,920,963 | 5/1990 | Brader | 128/402 |
| 5,300,099 * | 4/1994 | Rudie | 607/101 |
| 5,301,687 | 4/1994 | Wong et al. | 607/116 |
| 5,471,767 | 12/1995 | Walker | 36/2.6 |
| 5,649,973 | 7/1997 | Tierney et al. | 607/101 |
| 5,782,798 | 7/1998 | Rise | 604/49 |
| 5,800,486 | 9/1998 | Thome et al. | 607/105 |
| 5,938,692 * | 8/1999 | Rudie | 607/101 |
| 6,090,132 | 7/2000 | Fox | 607/96 |

\* cited by examiner

*Primary Examiner*—Linda C. M. Dvorak
*Assistant Examiner*—David M. Ruddy
(74) *Attorney, Agent, or Firm*—Marsh Fischmann & Breyfogle LLP

(57) ABSTRACT

A method and system to provide for the controlled heating of the preoptic anterior hypothalamus (POAH) for patients receiving such treatment. The system employs a catheter device which may be positioned proximate to the POAH and which emits radiant energy. The radiant energy provides for the heating of the POAH and a cooling apparatus may further be provide for cooling bodily tissues near the POAH which are heated. Feedback sensors may be positioned at various locations on the patient in order to determine an optimal position for the catheter device and to monitor the core body temperature. A control apparatus included with the system controls the amount of heating the POAH receives based on the feedback signals received from the sensors.

22 Claims, 4 Drawing Sheets

METHOD AND APPARATUS FOR PROVIDING LOCALIZED HEATING OF THE PREOPTIC ANTERIOR HYPOTHALAMUS

RELATED APPLICATIONS

This application claims priority under 35 U.S.C. § 119 to prior U.S. Provisional Patent Application Serial No. 60/099,965, filed on Sep. 11, 1998, and such prior application is hereby incorporated by reference in its entirety.

FIELD OF THE INVENTION

The invention relates to a method and system for providing localized heating of bodily tissues, and more particularly to a system and method for localized heating of the preoptic anterior hypothalamus (POAH).

BACKGROUND OF THE INVENTION

Stroke is one of the leading causes of death in adults and also a major cause of neurological disability. Until recently, stroke has been viewed as an untreatable event and all physicians could offer a stroke victim was rehabilitation to try to regain lost functions. In an effort to reduce the damage caused by strokes, a number of treatments have been proposed. In one interventional approach, known as neuroprotectant therapy, the intent is to limit the amount of neurological damage that occurs after the initial event. Neuroprotectant approaches includes the administration of several pharmacological agents and a treatment known as mild hypothermia, or a lowering of core body temperature by 2–4 degrees Celsius. The induction of mild hypothermia has been shown to inhibit several points of the chemical cascade that cause secondary cellular death after an ischemic event and to provide broad neuroprotection.

One method of inducing mild hypothermia is through heating of the preoptic anterior hypothalamus (POAH) which is located in the lower portion of the brain adjacent to the skull. It is known that the POAH is the thermostat for sensing core body temperature and controlling thermo regulatory responses in animals. The cooling mechanisms elicited by the POAH include reduction of metabolic energy generation, vasodilatation enhancing skin cooling, and sweating. Full vasodilatation can increase the rate of heat transfer to the skin as much as eight fold. An additional one degree Celsius It is known that the POAH is the thermostat for sensing core body temperature and controlling thermo regulatory responses in animals. The cooling mechanisms elicited by the POAH include reduction of metabolic energy generation, vasodilatation enhancing skin cooling, and sweating. Full vasodilatation can increase the rate of heat transfer to the skin as much as eight fold. An additional one degree Celsius increase in body temperature can increase sweating enough to remove ten times the basal rate of heat protection.

SUMMARY OF THE INVENTION

For a patient receiving treatment, it has been recognized that if particular forms of radiant energy, such as microwave energy, are emitted from locations proximate to the POAH, localized heating of the POAH may be provided. It has been further recognized that heating of the POAH may also cause heating in bodily tissues which surround the POAH, and as such, a cooling may be provided for said tissues.

In order to induce the desired heating in the POAH, a catheter device configurable to emit radiant energy at a selected magnitude may be provided. The catheter device may be further configured to be positionable at a desired location with regards to the POAH. A cooling apparatus may be employed in conjunction with the catheter device to provide cooling for surrounding bodily tissues.

In operation, the catheter device may be initially positioned at the desired location proximate to the POAH. Once positioned, predetermined amounts of radiant energy may then be emitted from the catheter device at the POAH. While the POAH is being heated, the cooling apparatus may be activated and the surrounding bodily tissues cooled.

In one aspect of the invention, the catheter device may be routed through the nasal cavity of the patient into the sphenoidal sinus. Once the catheter device is positioned, radiant energy may be emitted, heating the POAH. Upon application of the heat, the POAH may begin initiating thermoregulatory cooling processes for the patient such as reduction in metabolic energy generation, vasodilatation, and sweating which act to reduce the core body temperature.

In another aspect of the invention, the catheter device and connecting electronics may be configured such that microwave radiation is employed as the radiant energy. A waveguide may run from a microwave oscillator and power source, to an antennae incorporated in the catheter device. A control device may be further connected to the oscillator to provide for manual or automated control of the magnitude of radiant energy emitted through the antennae.

As was described above, the system described herein may further include a cooling apparatus. As part of this cooling apparatus, the catheter device may include a bladder-like structure through which a coolant, such as a liquid or gas, may be circulated. A reservoir of coolant may be remotely located, and a pump may be employed to circulate coolant through the bladder. When the coolant is pumped, the bladder may expand and contact bodily tissues which are in close proximity to the catheter device, and the coolant circulated through the bladder may provide cooling for said tissues. The amount of cooling may be varied by changing the temperature or rate of circulation of the coolant.

The system described herein may further include a number of sensors which may be employed to control the heating process. These sensors may take measurements at designated locations and provide feedback signals which may be used to vary the amount of radiant energy emitted by the catheter device. A first condition which may be detected by a sensor is skin conductivity. This measurement may provide an indication of the amount a patient is sweating when the thermoregulatory cooling processes are initiated. Electrodes may be placed at a selected location on the skin surface of the patient and measurements taken across the electrodes.

The skin conductivity measurement may be employed in situations where the optimal location for positioning the catheter is sought. Because the microwave energy emitted from the antennae may have directional sensitivity, the catheter device requires positioning in order to identify an optimal transmission location. To find this optimal location, the catheter device may be initially positioned in the sinus cavity and radiant energy emitted from the catheter device at a low magnitude. As the POAH initiates the cooling processes for the body, measurements may then be taken of the skin conductivity as the position of the catheter device in the sphenoidal sinus is varied. When the maximum skin conductivity is detected (i.e., the greatest amount of sweating is detected), the optimal location for the catheter device may be determined.

One purpose of the system described herein is to lower the core body temperature of the patient to a desired level. As such, a sensor may be employed to monitor the core body temperature of the patient. This sensor may be located on an area of the patient which provides indications of the body core temperature, such as the tampanic membrane, esophageal, or nasopharyngeal. Feedback signals received by the control module from the temperature sensor may be employed to vary the amount of radiant energy emitted from the catheter device which in turn varies the core body temperature.

The core body temperature may come into use after the catheter device has been optimally positioned and the process for lowering the core body temperature is begun. The magnitude of the radiant energy may be increased to provide heating of the POAH so as to induce mild hypothermia. As the heating progresses, the POAH further initiates the thermoregulatory cooling processes.

As the core body temperature decreases, this is detected by the core body temperature sensor. Because the cooling of the core body temperature may also acts to cool the POAH, the magnitude of the radiant energy emitted from the catheter device may need to be increased as core temperature drops. When the desired drop in core temperature is achieved, this condition may be monitored and automatically maintained by the system described herein. the control module may make the necessary changes in radiant energy output and/or cooling in order to maintain the desired core body temperature.

After the core body temperature has been lowered for the desired period of time, the above process may be reversed such that the magnitude of radiant energy is decreased and the core body temperature is raised at a predetermined rate.

These and other aspects and related advantages of the present invention should become apparent from a review of the following detailed description when taken in conjunction with the accompanying figures.

DETAILED DESCRIPTION

Figure 1:
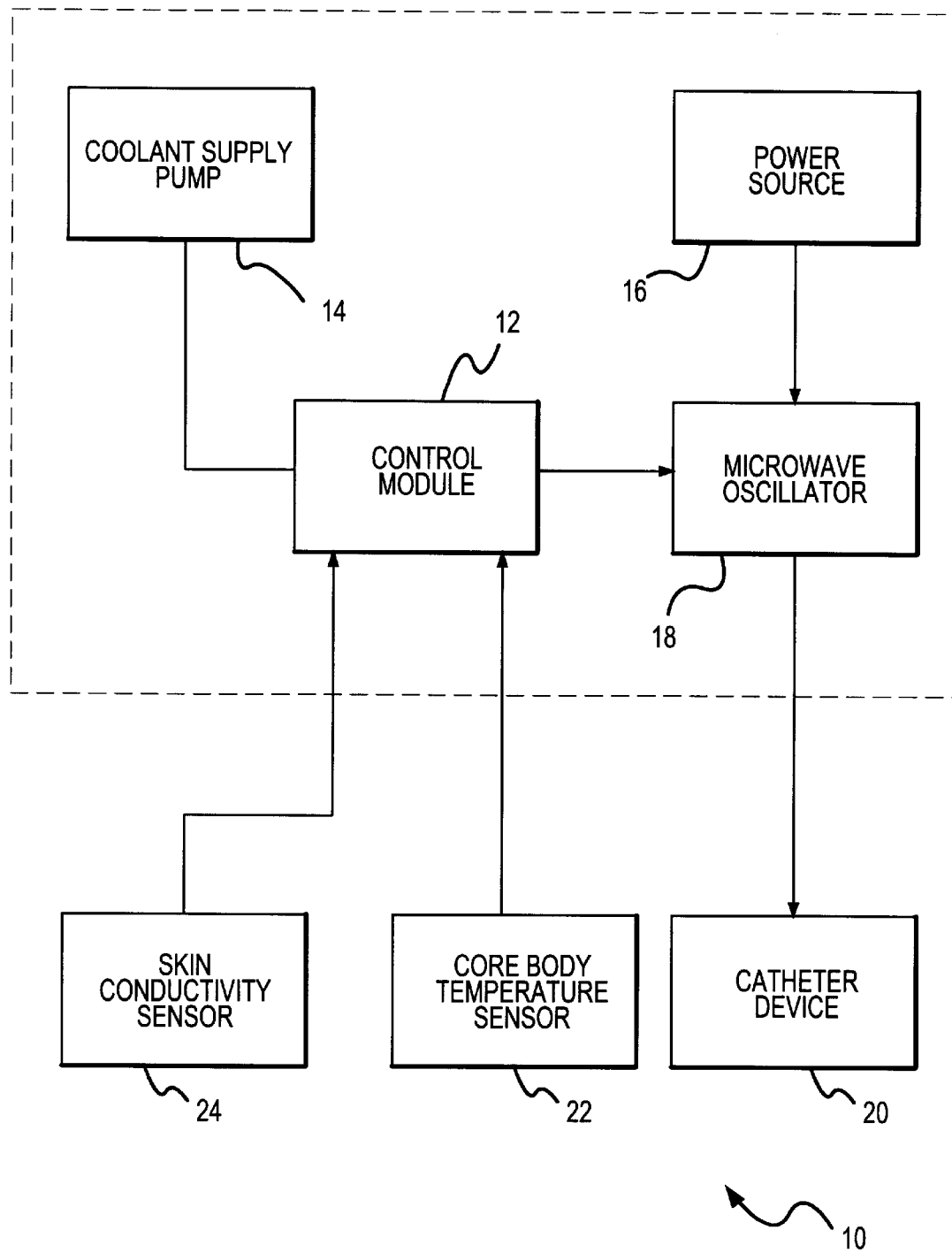
FIG. 1 discloses a diagram for the heating system described herein.

Disclosed in FIG. 1 is a diagram for the system described herein. One application of the system is the heating of the preoptic anterior hypothalamus (POAH) through the exposure of the POAH to a source of radiating energy. It is known that heating of the POAH may induce mild hypothermia in patients receiving the treatment. The system includes a catheter device 20, which is sized such that it may be positionable proximate to the POAH, such as within the sphenoidal sinus . The catheter device may further include an internal antenna for emitting radiant energy. The detailed configuration of the catheter device will be described in greater detail below.

One type of radiant energy which may be emitted from the catheter device may be microwave radiation. As such, a connection is established between the catheter device and oscillator 18. The oscillator described herein is variable such that it may emit radiant energy over the entire microwave range (300 GHz–300 MHZ). In connection with the oscillator 18 is power source 16, which provides the necessary power in order to generate the radiant energy signals.

In connection with the oscillator 18 is the control module 12. The control module includes programming for directing the output of the oscillator in response to various external inputs. This control module may comprise any number of electronic devices (such as a personal computer) which provide automatic monitoring and control functions. This module includes the necessary computational power to measure incoming control signals and in response provide command signals for directing the operations of external components.

In the system disclosed in FIG. 1, feedback signals are provided to the control module 12 through the skin conductivity sensor 24 and the core body temperature sensor 22. The skin conductivity sensor 24 may include a number of electrodes which may be positioned on various locations of the skin. As the amount of liquid (such as sweat) accumulates on the skin surface, the conductivity will increase. Such conductivity sensors are well know and commercially available.

Also connected to the control module 12 is the core body temperature sensor 22. This temperature sensor, may be attached to a number of body parts which are known to provide an accurate indication of core body temperature. These locations may include the tampanic membrane, esophageal, or nasopharyngeal regions. The sensor generates an electric signal whose magnitude is indicative of the temperature measured. Such temperature sensor are known to one skilled in the art and are commercially available.

Also attached to the control module 12 is the coolant supply pump 14. As will be described in greater detail below, the catheter device 20 includes an apparatus for cooling tissue regions proximate to the catheter device which are exposed to the radiant energy. The amount of cooling provided to the catheter device may be changed by varying the pressure or the temperature of the coolant which is circulated through the catheter device. Alternatively, or in conjunction with, the control module may be connected to an adjustable valve, which may be opened or closed depending on the desired pressure for the coolant within the system.

The system disclosed in FIG. 1 has a particular usefulness in providing a treatment for victims of strokes. It has been discovered that the effects of a stroke may be reduced if a mild hypothermia is induced in the victim of the stroke soon after the stroke has incurred. The induction of mild hypothermia has been shown to inhibit several points of the chemical cascade that causes secondary cellular death after an ischemic event and to provide broad neuroprotection.

One method of inducing mild hypothermia in a stroke patient is to provide localized heating of the POAH. As is well known, the POAH is a thermostat for sensing core body temperature and controlling thermal regulatory responses in mammals. The POAH is located in the lower portion of the brain adjacent to the skull. Local increases in POAH temperature can cause decreases in metabolic heat production (oxygen consumption), vasodilatation enhancing skin cooling, and sweating. Varying the temperature of the POAH is one method to vary the core body temperature of a patient.

Employing the system described herein, heating of the POAH is performed by directing radiant energy, such as microwaves, at the POAH. In order to achieve this heating, the catheter device may be positioned near or proximate to the POAH, and radiant energy emitted toward the POAH. In order to locate the catheter device close to the POAH, it may be necessary to insert the catheter device into an interior cavity of the patient's head.

Figure 2:
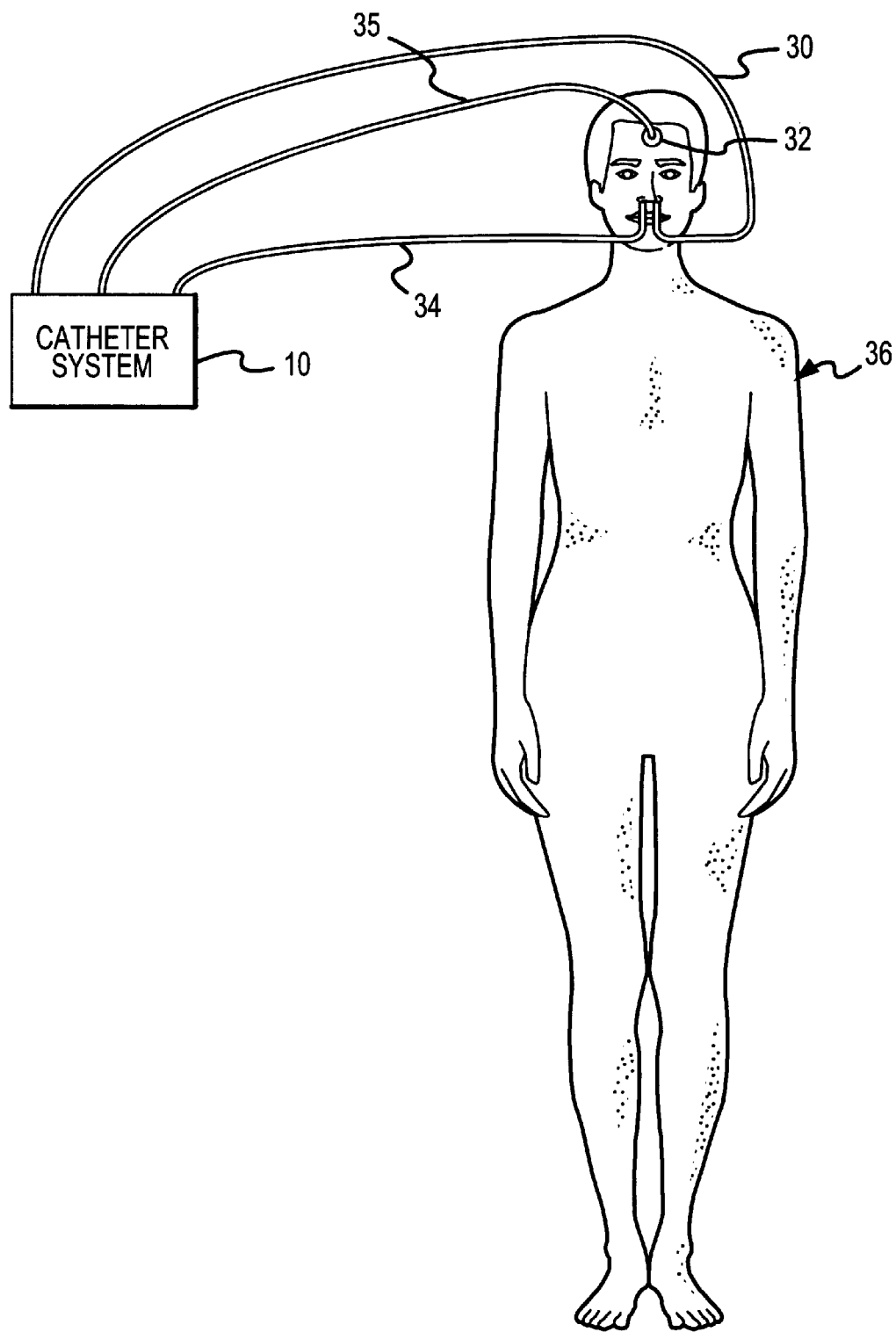
FIG. 2 discloses the placement of the sensors and the insertion of the catheter device in the nasal cavity.

Disclosed in FIG. 2 is a diagram which shows the system's 10 connections with regards to the patient 36 when heating of the POAH is to occur. Inserted in the nasal cavity of the cavity may be the core body temperature sensor (not shown). Running from the temperature sensor is feedback line 30 to the control system 10. The sensor is attached to a particular portion of the patient's anatomy which will provide an accurate core body temperature. Attached to the skin surface of the patient 36, is the skin conductivity sensor 32. Through this sensor, the conductivity of the skin may be measured across at least two electrodes. The signal provided by this sensor is indicative of the conductivity measurement and is fed back to the catheter system 10 for analysis along line 35.

The catheter device (not shown) is also placed in the nasal cavity of the patient 36. Line 34 provides a connection between the catheter device and the control system 10. Included in line 34 are the waveguide for carrying the radiant energy and conduits for carrying coolant. Upon insertion, a clinician may direct the catheter device to the proper location for emitting the radiant energy. This positioning process will be described in greater detail below.

Figure 3A:
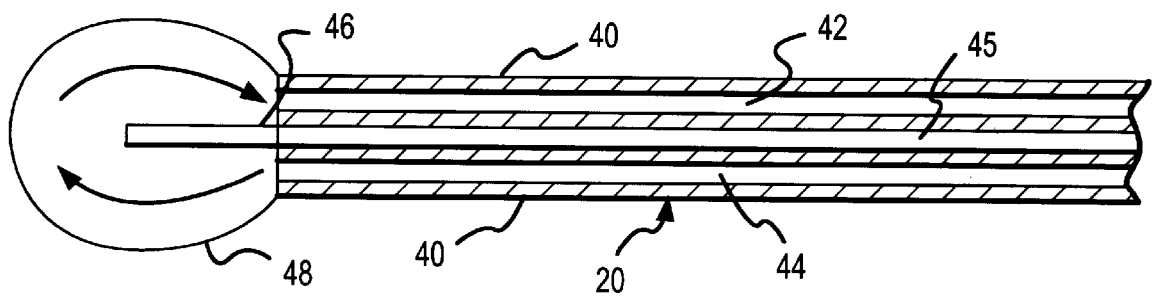
FIGS. 3a and b disclose cross sections of the catheter device.
Figure 3B:
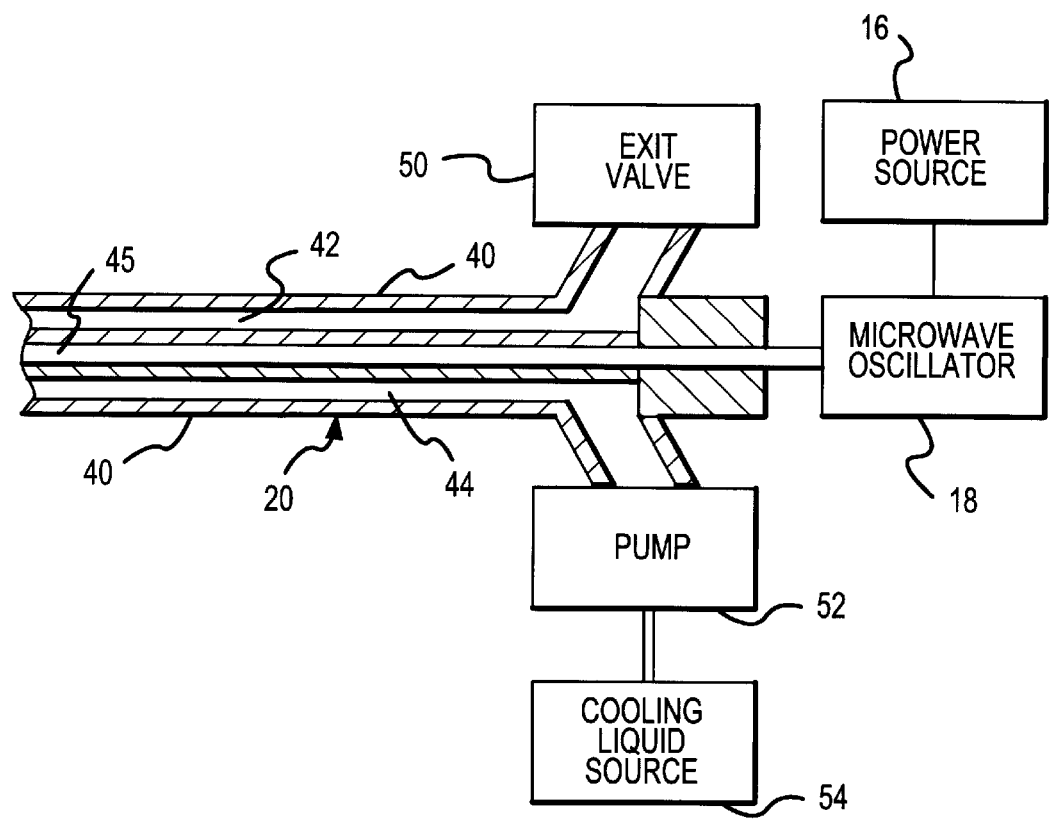

Disclosed in FIGS. 3A and 3B are detailed diagrams of the catheter device employed to emit the radiant energy. The catheter device is sized such that it may be inserted in the nasal cavity of the patient and directed into the sphenoidal sinus. Once in the sphenoidal sinus, the catheter device may be further positioned to emit radiant energy in an optimal fashion. Disclosed in FIG. 3a is the distal end of the catheter device which is employed to emit the radiant energy. Included in this portion of the catheter are the exterior body 40 which may be constructed of an electrically insulative material. Included within the body is conduit 44 which runs the length of the catheter device and is employed to carry coolant to the distal end of the catheter from a remotely located reservoir.

Also at the distal end of the catheter is a bladder type device 48 into which the coolant may circulate. Enclosed within the bladder 48 is the microwave antenna 46 which provides for the emission of the radiant energy. Running through the body of the catheter device to the antenna 46 is waveguide 45. Waveguide 45 may be a co-axial cable which transports microwave signals from the oscillator to the antennae. Also incorporated in the catheter body is return conduit 42 which acts to carry the coolant from the bladder 48 to a remotely located reservoir.

Disclosed in FIG. 3B are the connections established from the catheter device to the various systems which either provide the radiant energy or provide for the circulation of coolant. Cooling source 54 may comprise a reservoir of coolant, wherein the coolant may comprise either a liquid or a gas. Pump 52 acts to pump the coolant into conduit 44 such that it may be circulated within the bladder device. Conduit 42 provides a return path for the coolant which then exits the system through exit valve 50. The coolant may then be disposed of or circulated in a reservoir and used again. A connection is also established between waveguide 45 and oscillator 18. The oscillator is adjustable such that it can provide a range of radiant energy signals which may be transported to the antennae. Power for generating the radiant energy signals is provided by power source 16.

In operation, prior to the emission of any radiant energy to heat the POAH, the temperature sensor and conductivity catheter devices are first positioned on the patient. The skin conductivity catheter device may be attached to any exterior skin surface of the patient, however to provide an optimal reading, the electrodes may be positioned somewhere about the head region. The core body temperature sensor may be placed on any bodily region which would provide an accurate indication of the core body temperature. These portions of the body include the tampanic membrane, esophageal or the nasopharyngeal.

Figure 4:
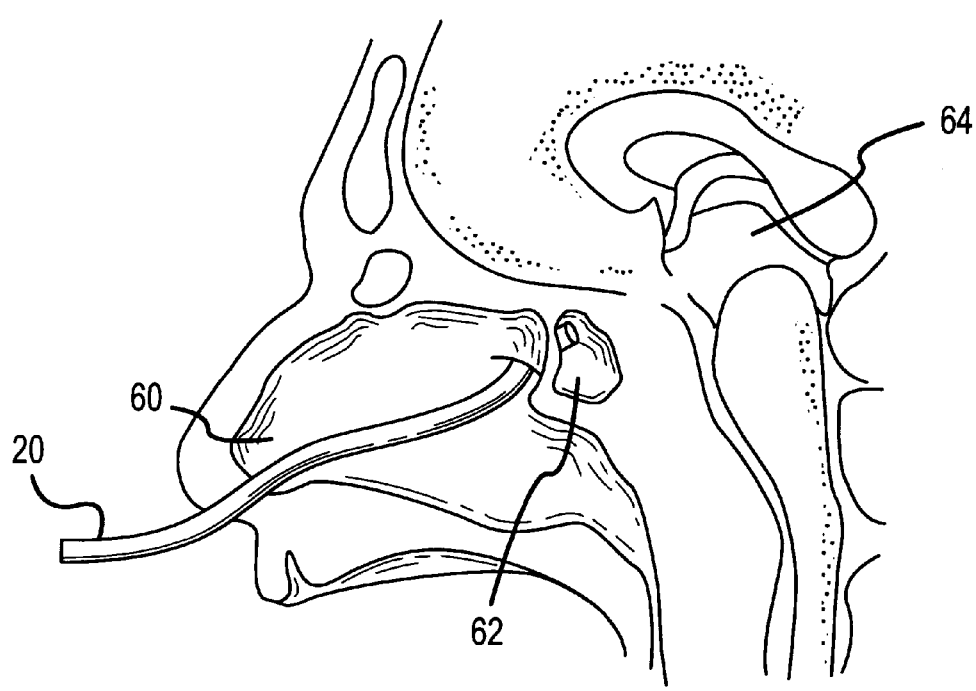
FIG. 4 discloses the location for the placement of the catheter device in the sinus cavity.

At this point, the catheter device may be inserted into the patient's body. In positioning the catheter device it is desirable to find a location as close to the POAH as possible with a minimum of intervening tissue. One desirable location for positioning the catheter device is in the sphenoidal sinus cavity. Disclosed in FIG. 4 is a cross sectional view of the head region of a patient, which includes the nasal cavity 60. The catheter device 20 may be initially inserted through the nasal cavity and then routed up into the sphenoidal sinus cavity 62 to be as close to the POAH 64 as possible. Once the catheter is positioned within the cavity, the emission of radiant energy from the catheter device may begin.

Prior to the emission of radiant energy or simultaneously therewith, the cooling system incorporated into the catheter device as described above may be activated. The cooling system, through the pumping of the coolant into the bladder device, may expand said bladder to contact bodily tissues of the patient. Through this contact, cooling may be applied to the tissues and based on the temperature of the coolant, or the rate of circulation, a desired amount of cooling may be applied.

One initial procedure for applying radiant energy to the POAH, includes locating an optimal position for the radiant energy antenna. This may be done by a clinician through use of the skin conductivity sensor. While locating this optimal position, a low power radiant energy signal may be emitted from the antenna. The clinician then moves the antenna to different positions within the sphenoidal sinus cavity. Based on the heating provided, the POAH will initiate thermoregulatory cooling processes which includes sweating. The skin conductivity will change as a result of the hypothalamus sensing a minor, 0.25–0.5° Celsius increase in core temperature and initiate sweating as a primary response to the sensed core temperature rise. The optimal position for the catheter device corresponds with the maximum conductivity detected by the sensors.

Once the catheter has been optimally positioned, the energy provided to the antenna may be increased to effect a desired (1–2° Celsius, for example) increase in POAH temperature. The body's natural reaction to the POAH warming will be to immediately reduce metabolic heat generation, vasodilatate, and generate sweat. At this time, the core body temperature will begin to drop.

The drop in core temperature will be sensed by the core temperature sensors and temperature signals will be fed back to the control system. The body's cooling process will also act to cool the POAH. As the core temperature sensor feeds back a signal to the control system that the temperature has dropped, the energy to the antenna would be increased proportionately, to maintain the POAH temperature above the physiologic set point. The absolute temperature of the POAH would not rise (due to the body's cooling effects being offset by the increased radiation) but the differential temperature between the POAH and surrounding tissue would increase. For some procedures, a core body temperature drop of up to 4° Celsius may be achieved without exceeding the maximum allowed temperature in the POAH realm or surrounding tissue.

One advantage of the system described herein is that through use of the cooling apparatus, heating the POAH may be achieved without overheating of the tissues which surround the POAH. The combination of radiant energy and conductive surface cooling results in a net rise in temperature deep within the brain tissue. It allows maximum net temperature within the tissue without damaging the tissue adjacent to the catheter.

Figure 5:
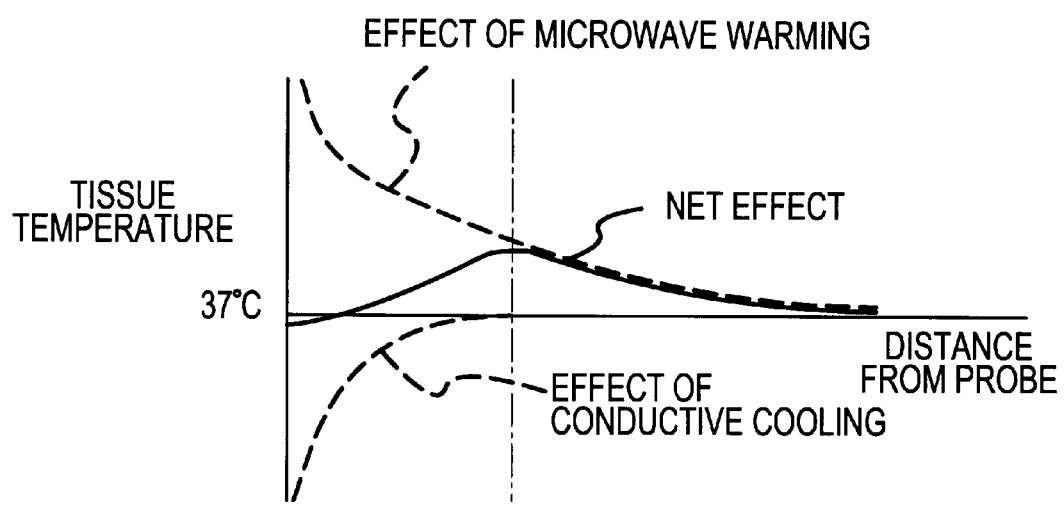
FIG. 5 discloses a graph which shows the effects of cooling the bodily tissues located between the catheter device and the POAH.

The effects of the combination of heating and cooling may be better understood by study of the graph in FIG. 5. Along the Y axis of the graph is the measured temperature with the tissue and the POAH, while along the X axis is the distance from the catheter device. As can be seen, without the conductive cooling, the effect of the microwave warming would cause a large rise in temperature to the tissues immediately adjacent to the microwave source. Through the effects of the conductive cooling, the maximum rise in temperature may be achieved at a desired distance from the microwave catheter device. In the application described herein, this maximal heating effect would coincide with the location of the POAH. Further, through varying of the cooling amounts, an extra measure of control may be provided for adjusting the temperature differential between the POAH and the surrounding tissue.

Once the desired temperature decrease has been achieved for the desired period of time, the energy provided to the microwave catheter may then be decreased at a selected rate to achieve a controlled increase in core temperature back to normal body temperature. Once the rise in temperature is complete, the catheter device and sensors may be removed from the patient.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant are, within the scope of the present invention. The embodiments described herein above are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A system for providing localized heating to the preoptic anterior hypothalamus (POAH) of a body comprising:
    a source of microwave radiation; and
    a catheter device which is connectable to the source of microwave radiation and is positionable inside a bodily cavity proximate to the POAH, wherein upon activation said catheter device emits predetermined amounts of microwave radiation to induce heating of the POAH;
    at least one sensor positionable at a predetermined location on the body, which provides feedback signals indicative of a temperature of the body;
        said at least one sensor includes at least one of: a core body temperature sensor positionable at a first predetermined location on the body which provides a first feedback signal indicative of the core body temperature of the body; and
        a skin conductivity sensor positionable at a second predetermined location on the body which provides a second feedback signal indicative of skin conductivity; and
    a controller connectable to the at least one sensor which controls power to the catheter device in an amount proportional to the magnitude of the feedback signal received from the at least one sensor.

2. The system of claim 1 further including cooling system positionable in the bodily cavity which provides cooling of tissues within a predetermined distance of the catheter device.

3. The system of claim 1 wherein the core body temperature sensor is attachable to at least one of: tampanic membrane, esophageal, and nasopharyngeal.

4. The system of claim 1 wherein the skin conductivity sensor comprises at least two electrodes attachable to an exterior skin surface of the body, across which the conductivity of bodily fluids emitted by the body are measurable.

5. A system for providing localized heating to the preoptic anterior hypothalamus (POAH) of a body comprising:
    a source of microwave radiation;
    a catheter device which is connectable to the source of microwave radiation and is positionable inside a bodily cavity proximate to the POAH, wherein upon activation said catheter device emits predetermined amounts of microwave radiation to induce heating of the POAH; and
    a cooling system incorporated in the catheter device, to provide a predetermined amount of cooling to the tissues located between the source of microwave energy and the POAH.

6. The system of claim 5 wherein the catheter comprises:
    a distal end which includes an antennae for emitting the microwave radiation;
    an insulative body which includes a waveguide for transporting the microwave radiation to the antennae from a remote source;
    an expandable bladder through which coolant may be circulated which encloses the antennae and is expandable when filled with the coolant; and
    at least one conduit incorporated into the insulative body for transporting the coolant to and from the expandable bladder.

7. The system of claim 6 wherein the catheter device is connectable to at least one of:
    a pumping device which pumps coolant from a reservoir;
    a valve device for controlling flow of the coolant leaving the catheter; and
    an oscillator and power source connectable to the conductor.

8. A method for heating the preoptic anterior hypothalamus (POAH) of a body comprising the steps of:
    positioning a source of microwave energy proximate to the POAH;
    emitting the microwave radiation from the catheter device toward the POAH; and providing a predetermined amount of cooling to the tissues located between the source of microwave energy and the POAH.

9. The method of claim 8 wherein the source of microwave radiation is a catheter device insertable in the nasal cavity and sphenoidal sinus region, wherein the catheter device includes a microwave antennae.

10. The method of claim 8 further comprising the step of measuring skin conductivity of skin to determine whether the source of microwave energy is located in an optimal position for emitting the microwave radiation.

11. The method of claim 8 further comprising the step of measuring core body temperature to control emission of the microwave radiation towards the POAH.

12. The method of claim 8 further comprising the step of pumping a coolant through the catheter device to provide cooling for the tissues.

13. The method of claim 12 wherein the coolant is pumped into a bladder device incorporated in the catheter device wherein the bladder device expands and contacts the tissues to which the cooling is provided.

14. The method of claim 10 wherein the microwave radiation is emitted at a first predetermined magnitude until the optimal position is determined.

15. The method of claim 14 wherein upon determination of the optimal position, the microwave radiation magnitude is increased to attain a desired amount of heating of the POAH.

16. The method of claim 13 wherein the cooling is varied to affect a differential temperature between the tissues and POAH.

17. A method of inducing mild hypothermia in a patient comprising the steps of:
   positioning a catheter device which emits microwave energy in the sphenoidal sinus region of the patient proximate to the preoptic anterior hypothalamus (POAH);
   emitting the radiant energy from the catheter device at a first predetermined level towards the POAH, such that the POAH is heated to a predetermined level so as to initiate a bodily thermoregulatory cooling response;
   periodically measuring the core body temperature; and
   automatically varying the microwave radiation emitted from the catheter to achieve a desired core body temperature indicative of mild hypothermia.

18. The method of claim 17 further comprising the step of cooling bodily tissues located between the catheter device and the POAH.

19. The method of claim 17 further including the steps of:
   upon positioning of the catheter device in the sphenoidal sinus, emitting the microwave radiation from the catheter device at a second predetermined level which is lower in magnitude than the first predetermined level;
   measuring skin conductivity; and
   repositioning the catheter device until a maximum reading of the skin conductivity is sensed.

20. The method of claim 17 further comprising the step of, after a designated period of time, decreasing the microwave radiation emitted from the catheter device at a predetermined rate to raise the core body temperature to a desired level.

21. The method of claim 17 wherein a temperature sensor to measure the core body temperature is attached to at least one of: tampanic membrane, esophageal, or nasopharyngeal.

22. The method of claim 18 wherein the cooling is varied to affect a differential temperature between the bodily tissues and the POAH.

* * * * *